(12) United States Patent
Tahara et al.

(10) Patent No.: US 7,400,702 B2
(45) Date of Patent: Jul. 15, 2008

(54) TIRE INSPECTION METHOD

(75) Inventors: Yuji Tahara, Kodaira (JP); Takahiro Goto, Soapedro (NL); Shigenobu Saigusa, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 11/763,003

(22) Filed: Jun. 14, 2007

(65) Prior Publication Data

US 2008/0056446 A1     Mar. 6, 2008

(30) Foreign Application Priority Data

Jun. 15, 2006   (JP)   .............................. 2006-166352

(51) Int. Cl.
G01B 15/06     (2006.01)
(52) U.S. Cl. .......................................... 378/61; 378/62
(58) Field of Classification Search .................... 378/58, 378/61, 62
See application file for complete search history.

(56) References Cited

FOREIGN PATENT DOCUMENTS

JP          6-341930 A    12/1994

*Primary Examiner*—Courtney Thomas
(74) *Attorney, Agent, or Firm*—Sughrue Mion, PLLC

(57) ABSTRACT

The electromagnetic radiation source arranged at the first position apart from the tire irradiates the electromagnetic radiation rays to the first and second points on the tire, respectively, and the first and second coordinates on the camera are acquired, the first and second coordinates corresponding to the first and second points, respectively. The electromagnetic radiation source moved from the first position to the second position along with an axial direction irradiates the electromagnetic radiation rays to the first and second points, respectively, and the third and fourth coordinates on the camera are acquired, the third and fourth coordinates corresponding to the first and second points, respectively. The coordinate of the first point is found by finding the intersection of the straight line connected between the first point and the first coordinate and the straight line connected between the second point and the third coordinate. At the same time, and the coordinate of the second point is found by finding the intersection of a straight line connected between the first position and the second coordinate and the straight line connected between the second position and the fourth coordinate. The real distance between the first point and the second point is calculated based on the coordinates of the first and second points. The length between the first point and the second point on the image is transformed into the real distance between the first point and the second point.

3 Claims, 3 Drawing Sheets

TIRE INSPECTION METHOD

TECHNICAL FIELD

The present invention relates to a tire inspection method for acquiring an image inside of a tire arranged between an electromagnetic radiation source and a camera at an opposed position of the electromagnetic radiation source and inspecting an arrangement of a belt cord (a steel cord) inside of the tire based on the acquired image.

RELATED ART

In a conventional tire inspection, as described in Japanese Patent Application Laid Open No. 341,930/1994, an inside of a tire is observed by observing an image of the tire acquired from a camera using an electromagnetic radiation ray such as an X-ray and a gamma ray.

However, in the conventional tire inspection, since the image acquired from the camera shows a width or a size of the tire larger than a real size of the tire in accordance with a principle of imaging, it is impossible to know a real distance between belt cords or a belt cord width inside of the tire. Therefore, since the tire width or the tire size on the image is different from a real tire width or a real tire size, it is difficult to improve a detection accuracy in a check with eyes or an automatic judgment of the tire.

DISCLOSURE OF THE INVENTION

The object of the present invention is to provide a tire inspection method which is capable of improving the detection accuracy in the check with eyes or the automatic judgment of the tire.

In an aspect of the present invention, there is provided a tire inspection method for acquiring an image inside of a tire arranged between an electromagnetic radiation source and a camera at an opposed position of the electromagnetic radiation source and inspecting an arrangement of a belt cord inside of the tire based on the acquired image; the method comprising steps of:

arranging the electromagnetic radiation source at a first position apart from the tire, irradiating electromagnetic radiation rays from the electromagnetic radiation source to first and second points on the tire, respectively, and acquiring first and second coordinates on the camera, the first and second coordinates corresponding to the first and second points, respectively;

moving the electromagnetic radiation source from the first position to a second position along with an axial direction, irradiating the electromagnetic radiation rays from the electromagnetic radiation source to the first and second points, respectively, and acquiring third and fourth coordinates on the camera, the third and fourth coordinates corresponding to the first and second points, respectively;

finding a coordinate of the first point by finding an intersection of a straight line connected between the first point and the first coordinate and a straight line connected between the second point and the third coordinate, and finding a coordinate of the second point by finding an intersection of a straight line connected between the first position and the second coordinate and a straight line connected between the second position and the fourth coordinate;

calculating a real distance between the first point and the second point based on the coordinates of the first and second points; and transforming a length between the first point and the second point on the image into a real distance between the first point and the second point.

When acquiring the image inside of the tire arranged between the electromagnetic radiation source and the camera at an opposed position of the electromagnetic radiation source and inspecting the arrangement of the belt cord inside of the tire based on the acquired image, it is necessary to correct the belt cord width or the size between the belt cords on the acquired image in order to acquire the real belt cord width of the belt cord and the real distance between the belt cords inside of the tire.

However, since a belt of the tire does not bend at a constant curvature but the belt at a central area of a tread extends in a horizontal direction and the curvature at an end of the tread is larger than that at the central area of the tread, the belt cord inside of the tire is not always arranged in the horizontal direction and the belt cord inside of the tire sometimes bends because of the tire size and the curvature of inner surface of the tire. Therefore, when correcting the belt cord width or the size between the belt cords, a correction using a similarity of a triangle is not effective if the belt cord inside of the tire is not arranged in the horizontal direction.

According to the present invention, there are (1) to (5) steps in the following.

(1) The electromagnetic radiation source arranged at the first position apart from the tire irradiates the electromagnetic radiation rays to the first and second points on the tire, respectively, and the first and second coordinates on the camera are acquired, the first and second coordinates corresponding to the first and second points, respectively.

(2) The electromagnetic radiation source moved from the first position to the second position along with an axial direction irradiates the electromagnetic radiation rays to the first and second points, respectively, and the third and fourth coordinates on the camera are acquired, the third and fourth coordinates corresponding to the first and second points, respectively.

(3) The coordinate of the first point is found by finding the intersection of the straight line connected between the first point and the first coordinate and the straight line connected between the second point and the third coordinate, and the coordinate of the second point is found by finding the intersection of a straight line connected between the first position and the second coordinate and the straight line connected between the second position and the fourth coordinate.

(4) The real distance between the first point and the second point is calculated based on the coordinates of the first and second points.

(5) The length between the first point and the second point on the image is transformed into the real distance between the first point and the second point.

In this way, by radiating the electromagnetic radiation rays from the first and second positions and finding the first and second points from the intersections between the electromagnetic radiation rays from the first position and that from the second position, it is possible to calculate the real distance between the first point and the second point in consideration of a degree of inclination of the belt even in the end of the tread with the high curvature. As a result, it is possible to improve the detection accuracy in the check with eyes or the automatic judgment of the tire.

When the first point is one end of the belt cord and the second point is the other end of the belt cord, it is possible to calculate the real belt cord width. When the first point is one end of the belt cord and the second point is one end of another belt cord neighboring to one end of the belt cord, it is possible to calculate a step of two belt ends that is a distance between the two belt cord ends with different width from each other.

BEST MODE FOR CARRING OUT THE INVENTION

A preferred embodiment of the tire inspection method according to the invention is described with reference to accompanying drawings.

Figure 1:
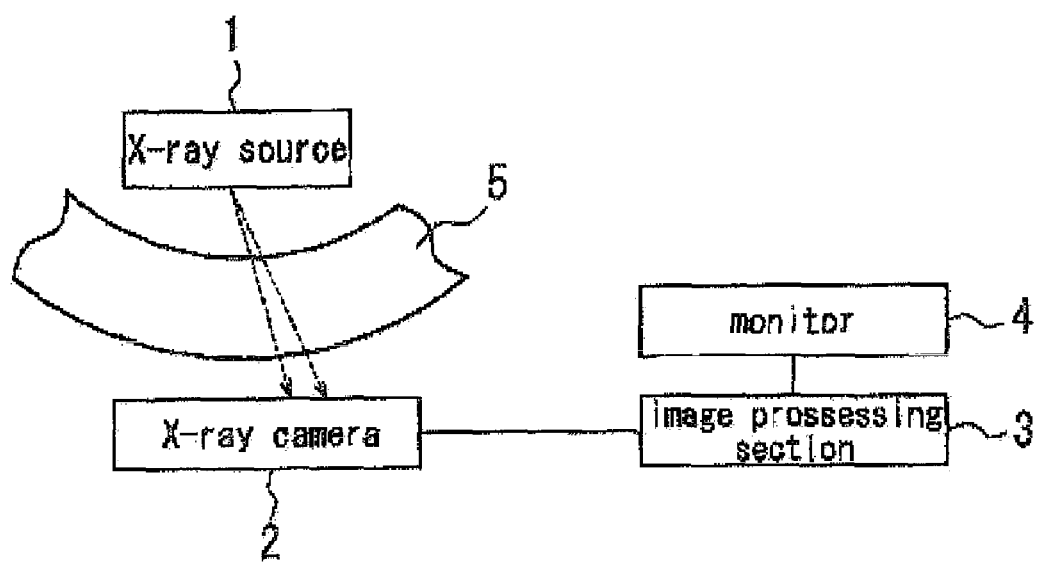
FIG. 1 is a diagram showing a tire inspection apparatus carrying out the tire inspection method according to the present invention.

FIG. 1 is a diagram showing a tire inspection apparatus carrying out the tire inspection method according to the present invention. The tire inspection apparatus comprises an X-ray source 1, X-ray camera 2, an image processing section 3 and a monitor 4.

The X-ray source 1 is movable along a y-axis direction of a three-dimensional coordinate system (The y-axis direction corresponds to a horizontal direction.) and irradiates an X-ray to a tire 5 to be inspected. The X-ray through the tire 5 is incident on the X-ray camera 2 and the X-ray camera 2 acquires an image of a tire 5 to be inspected. The image processing section 3 processes the acquired image as described later and the processed image is output to the monitor 4.

Figure 2:
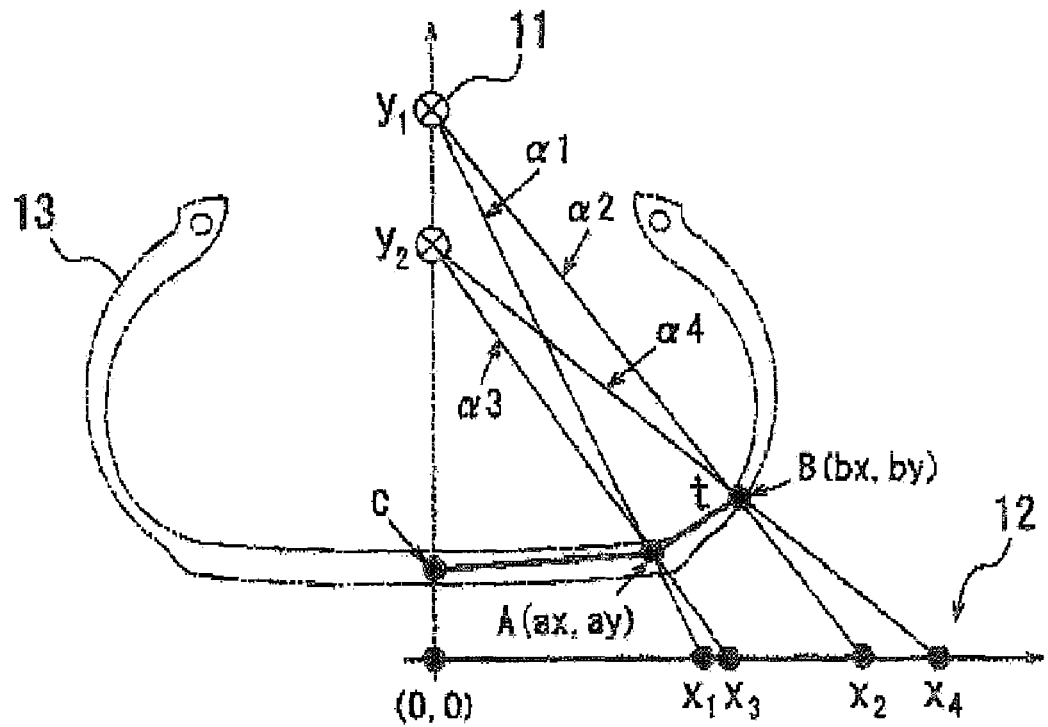
FIG. 2 is a diagram explaining the tire inspection method according to the present invention.
Figure 3:
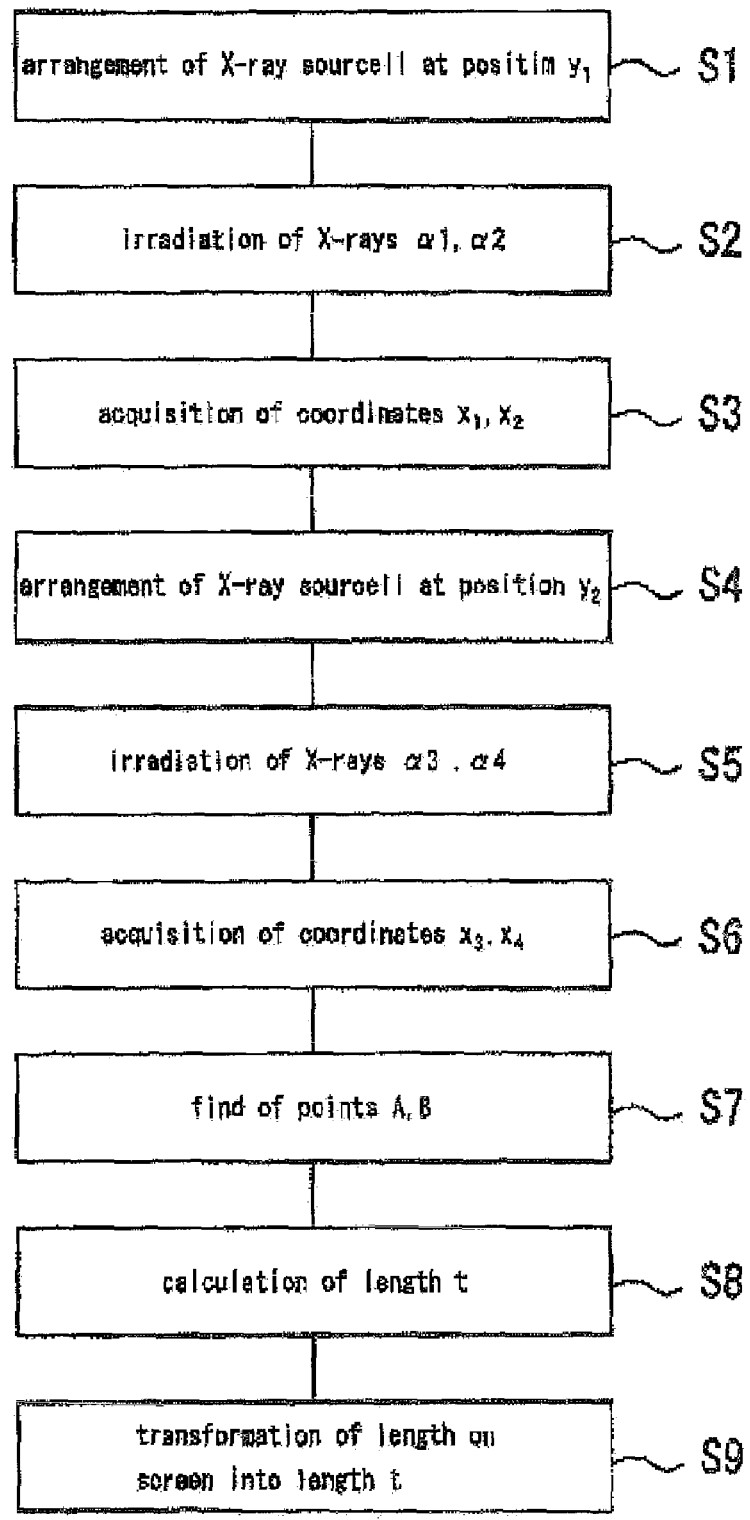
FIG. 3 is a flow chart of steps of the tire inspection method according to the present invention.

FIG. 2 is a diagram explaining the tire inspection method according to the present invention and FIG. 3 is a flow chart of steps of the tire inspection method according to the present invention. These steps are to acquire an image inside of a tire 13 arranged between an X-ray radiation source 11 and a X-ray camera 12 at an opposed position of the X-ray radiation source 11 and to inspect an arrangement of a belt cord inside of the tire 13 based on the acquired image. At first, in Step S1, the X ray source 11 is arranged on a position of an x-y coordinate $(0, y1)$.

Next, the x-ray source 11 irradiates radiation rays $\alpha 1$, $\alpha 2$ to points A, B of the tire 13, respectively (Step S2), and an x-y coordinates $(x1, 0)$, $(x2, 0)$ on the camera 12 is acquired (Step S3), the x-y coordinates $(x1, 0)$, $(x2, 0)$ corresponding to the points A, B, respectively. Next, the X-ray source 11 is arranged on a position of an x-y coordinate $(0, y2)$ (Step S4), the x-ray source 11 irradiates radiation rays $\alpha 3$, $\alpha 4$ to the points A, B of the tire 13, respectively (Step S5), and an x-y coordinates $(x3, 0)$, $(x4, 0)$ on the camera 12 is acquired (Step S6), the x-y coordinates $(x3, 0)$, $(x4, 0)$ corresponding to the points A, B, respectively.

When acquiring the x coordinates x1 to x4, points of reference (marks) of an object to be measured (in the embodiment, the points A, B) are determined and the coordinates are calculated from the X-ray 12 camera acquiring the marks. Therefore, when the point A is one end of the belt cord and the point B is the other end of the belt cord, it is possible to calculate the real belt cord width. On the other hand, the point A is one end of the belt cord and the point B is one end of another belt cord neighboring to one end of the belt cord, it is possible to calculate a step of two belt ends that is a distance between the two belt cord ends with different width from each other. For an object having no points of reference (mark) of metal, it is possible to find the x coordinates x1 to x4 by preliminarily fixing a metal piece to an inclined portion of an object to be inspected. Further, a point C which is an intersection of a y-axis and the tire 13 is known and the x-y coordinate on the X-ray camera 12 corresponding to the point C is $(0, 0)$.

Next, an x-y coordinate $(ax, ay)$ of the point A is found by finding an intersection of the radiation ray $\alpha 1$ (which is a straight line connected between the x-y coordinate $(0, y1)$ and the x-y coordinate $(x1, 0)$) and the radiation ray $\alpha 3$ (which is a straight line connected between the x-y coordinate $(0, y2)$ and the x-y coordinate $(x3, 0)$), and an x-y coordinate $(bx, by)$ of the point B is found by finding an intersect of the radiation ray $\alpha 2$ (which is a straight line connected between the x-y coordinate $(0, y1)$ and the x-y coordinate $(x2, 0)$) and the radiation ray $\alpha 4$ (which is a straight line connected between the x-y coordinate $(0, y2)$ and the x-y coordinate $(x4, 0)$). (Step S7).

Next, a real length t between the point A and the point B is calculated (Step S8). The distance t becomes $\{(ax-bx)^2+(ay-by)^2\}^{1/2}$. At the end, the distance between the point A and the point B on the image is transformed into the length t.

Figure 4:
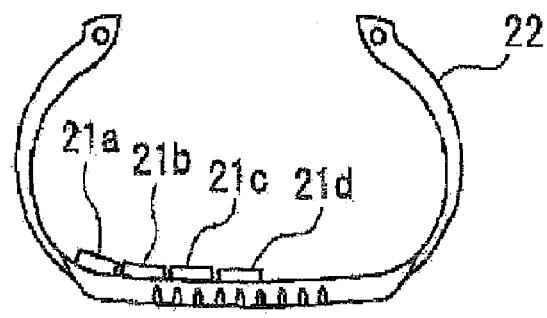
FIG. 4 is a diagram explaining an experiment of the tire inspection method according to the present invention.

Hereinafter, an experimental result of the tire inspection method according to the present invention will be explained. An experiment was carried out where four belt cords 21a, 21b, 21c and 21d with 12.4 mm width were arranged inside of a tire 22. (Refer to FIG. 4) In this case, a belt cord width to be imaged was a multiplication of the number of pixels and the pixel width occupied by the belt cord to be imaged. (The multiplication of the number of pixels and the pixel width corresponded to 4 mm.)

Figure 5:
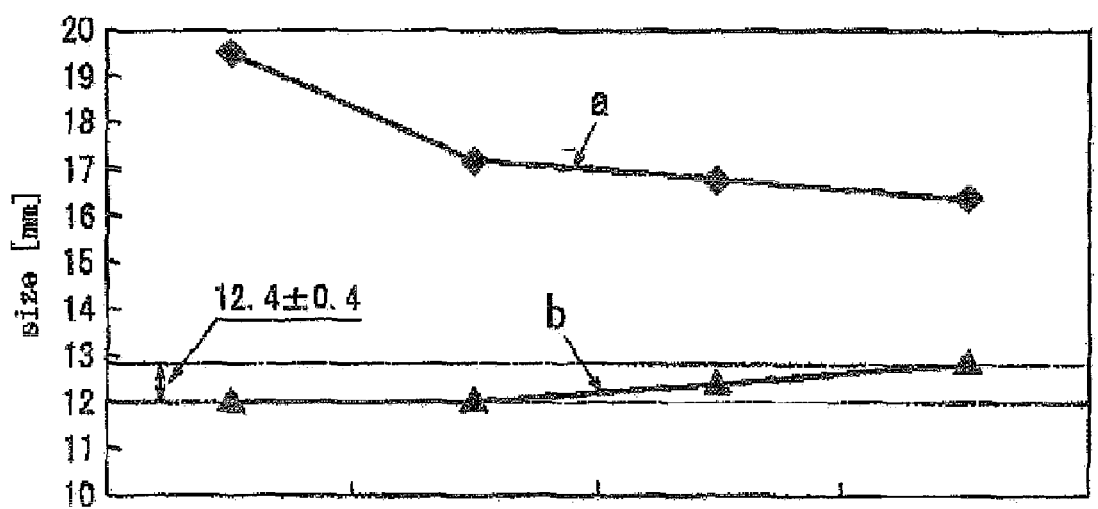
FIG. 5 is a diagram showing an experimental result of the tire inspection method according to the present invention.

FIG. 5 is a diagram showing an experimental result of the tire inspection method according to the present invention. The four belt cord widths to be imaged were 19.6 mm, 17.2 mm, 16.8 mm and 16.4 mm, respectively, as shown in a line a of FIG. 5. By correcting four belt cord widths to be imaged with the tire inspection method according to the present invention, the four belt cord widths to be imaged were transformed into 12.0 mm, 12.00, 12.4 m and 12.8 mm, respectively as shown in a line b of FIG. 5. Therefore, the four belt cord widths as shown in the line b substantially corresponded to real belt cord widths, respectively.

While the preferred embodiment of the present invention is explained with reference to the accompanying drawings, many changes and many modifications may be made without departing from the scope of the invention.

For example, other kinds of the electromagnetic radiation ray such as gamma ray may be used instead of the X-ray.

The invention claimed is:

1. A tire inspection method for acquiring an image inside of a tire arranged between an electromagnetic radiation source and a camera at an opposed position said electromagnetic radiation source and inspecting an arrangement of a belt cord inside of said tire based on the acquired image; said method comprising steps of:

arranging said electromagnetic radiation source at a first position apart from said tire, irradiating electromagnetic radiation rays from said electromagnetic radiation source to first and second points on said tire, respectively, and acquiring first and second coordinates on said camera, said first and second coordinates corresponding to said first and second points, respectively;

moving said electromagnetic radiation source from said first position to a second position along with an axial direction, irradiating the electromagnetic radiation rays from said electromagnetic radiation source to said first and second points, respectively, and acquiring third and fourth coordinates on said camera, said third and fourth coordinates corresponding to said first and second points, respectively;

finding a coordinate of said first point by finding an intersection of a straight line connected between said first point and said first coordinate and a straight line connected between said second point and said third coordinate, and finding a coordinate of said second point by finding an intersection of a straight line connected between said first position and said second coordinate and a straight line connected between said second position and said fourth coordinate;

calculating a real distance between said first point and said second point based on the coordinates of said first and second points; and transforming a length between said first point and said second point on said image into a real distance between said first point and said second point.

2. The method according to claim 1, wherein said first point is one end of said belt cord and said second point is the other end of said belt cord.

3. The method according to claim 1, wherein said first point is one end of said belt cord and said second point is one end of another belt cord neighboring to one end of said belt cord.

* * * * *